(12) United States Patent
Sugiyama et al.

(10) Patent No.: US 7,067,622 B2
(45) Date of Patent: Jun. 27, 2006

(54) METHOD OF THE SOLID PHASE SYNTHESIS OF PYRROLE-IMIDAZOLE POLYAMIDE

(75) Inventors: Hiroshi Sugiyama, Tokyo (JP); Hirokazu Iida, Tokushima (JP); Isao Saito, Kyoto (JP); Takashi Saito, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 22 days.

(21) Appl. No.: 10/481,275

(22) PCT Filed: Feb. 27, 2002

(86) PCT No.: PCT/JP02/01775

§ 371 (c)(1),
(2), (4) Date: Dec. 19, 2003

(87) PCT Pub. No.: WO03/000683

PCT Pub. Date: Jan. 3, 2003

(65) Prior Publication Data

US 2004/0171799 A1 Sep. 2, 2004

(30) Foreign Application Priority Data

Jun. 25, 2001 (JP) ............................. 2001-190957

(51) Int. Cl.
C07K 1/02 (2006.01)
(52) U.S. Cl. .................................................. 530/333
(58) Field of Classification Search ................. 530/333
See application file for complete search history.

(56) References Cited

U.S. PATENT DOCUMENTS

| | | | |
|---|---|---|---|
| 6,545,162 B1 * | 4/2003 | Dervan et al. ............ | 548/312.1 |
| 6,566,336 B1 * | 5/2003 | Sugiyama et al. ............ | 514/18 |
| 6,713,633 B1 * | 3/2004 | Sugiyama et al. .......... | 548/416 |
| 6,777,425 B1 * | 8/2004 | Burli .......................... | 514/307 |

FOREIGN PATENT DOCUMENTS

| JP | 2001-136974 | 5/2001 |
|---|---|---|
| WO | WO 97/23496 A1 | 7/1997 |
| WO | WO 97/27327 A1 | 7/1997 |
| WO | WO 97/30975 A2 | 8/1997 |
| WO | WO 98/37066 A1 | 8/1998 |
| WO | WO 98/45284 A1 | 10/1998 |
| WO | WO 98/49142 A1 | 11/1998 |

OTHER PUBLICATIONS

Tao et al. Rational Design of Sequence-Specific DNA Alkylating Agents Based on Duocarmycin A and Pyrrole-Imidazole Hairpin Polyamides. J. Am. Chem. Soc. 1999, vol. 121, pp. 4961-4967.*

Saito et al., "Fmoc Solid-Phase Synthesis of Pyrrole-Imidazole Polyamides," Organics, vol. 79, Kanto Reagents (Mar. 2001).

Baird et al., "Solid Phase Synthesis of Polymides Containing Imidazole and Pyrrole Amino Acids," Journal of the American Chemical Society, vol. 118, pp. 6141-6146, American Chemical Society (1996).

Vazquez et al., "An Fmoc Solid-Phase Approach to Linear Polypyrrole-Peptide Conjugates," Tetrahedron Letters, vol. 40, pp. 3621-3624, Elsevier Science Ltd. (1999).

Satz et al., "Recognition of Nine Base Pairs in the Minor Groove of DNA by a Tripyrrole Peptide-Hoechst Conjugate," Journal of the American Chemical Society, vol. 123, No. 11, pp. 2469-2477, American Chemical Society (Mar. 21, 2001).

International Search Report.

International Preliminary Examination Report.

Cho et al., "Cyclic Polyamides for Recognition in the Minor Groove of DNA," Proceedings of the National Academies of Science USA—Chemistry, vol. 92, pp. 10389-10392 (Oct. 1995).

Xiao et al., "A Convenient Method for the Synthesis of DNA-Recognizing Polyamides in Solution," Journal of Organic Chemistry, vol. 65, No. 18, pp. 5506-5513, American Chemical Society (2000).

Wurtz et al., "Fmoc Solid Phase Synthesis of Polyamides Containing Pyrrole and Imidazole Amino Acids," Organic Letters, vol. 3, No. 8, pp. 1201-1203, American Chemical Society (2001).

* cited by examiner

Primary Examiner—Christopher R Tate
Assistant Examiner—Marcela M Cordero Garcia
(74) Attorney, Agent, or Firm—Rader, Fishmen & Grauer PLLC

(57) ABSTRACT

It is intended to provide a method of producing a pyrrole-imidazole polyamide whereby a longer pyrrole-imidazole polyamide can be conveniently synthesized and a peptide (protein) can be easily transferred. According to this method, a pyrrole-imidazole polyamide having a carboxylate group which can be excised from a solid phase carrier at its end, makes it possible to directly transfer various functional groups and can exactly distinguish DNA sequences can be efficiently produced. A method of synthesizing a pyrrole-imidazole polyamide characterized by performing automatic synthesis by the solid phase Fmoc method with the used of a peptide synthesizer; a pyrrole-imidazole polyamide having a carboxyl group at its end obtained by this method; a pyrrole-imidazole polyamide having a DNA alkylation agent transferred into the carboxyl group at the end of the above-described pyrrole-imidazole polyamide; and a sequence-specific DNA alkylation method characterized by using the above compound.

12 Claims, 3 Drawing Sheets

METHOD OF THE SOLID PHASE SYNTHESIS OF PYRROLE-IMIDAZOLE POLYAMIDE

TECHNICAL FIELD

The present invention relates to a novel method of synthesizing pyrrole-imidazole polyamide which is being noted as a useful compound for controlling a gene expression as a result of recent active researches which have clarified that the compound can be combined with a DNA in a sequence-specific manner.

BACKGROUND ART

As a result of recent active genome analyses and studies, a clarification of the human genome constituted of a sequence of about 3 billions of deoxyribo nucleic acids (DNA) has almost been accomplished. The trend is now shifting to discoveries and clarifications of genes which are sources of gene information and, further, to clarifications of single-nucleotide polymorphisms (SNPs) which affect the physical constitution of individuals. Various genes and gene information have been clarified by the studies, and synthesis of a compound which controls the gene information in a specific manner is considered to be a useful process of a drug discovery technology of new era.

The present inventors have focused and have been studying on distamycin, an antibiotic, which is known to selectively bond to a site of a DNA abundant with AT base pairs. As a part of the study, the inventors have synthesized systematic distamycin derivatives by combining a pyrrole amide which is a constituent unit of distamycin and an imidazole amide which is a derivative of the pyrrole amide and has been conducting biochemical researches on the thus-obtained compounds. As a result of the researches, the inventors have clarified that each of the compounds is capable of selectively bonding with a specific site of DNA and the selectivity is defined by an order of pyrrole amide (Py) and imidazole amide (Im).

Further, the inventors have found a systematic screening method for conducting a cytotoxicity test on the known cancer cells by using the synthesized pyrrole-imidazole polyamides. This method is a simultaneous and easy screening method of the compounds targeting on DNA sequence specific to a certain cancer cell, which DNA sequence is being clarified in the human genome project. In the case where the number of pyrrole-imidazole amides, which are the constituent units, is 8, there are 256 combinations. By screening those compounds simultaneously, it is possible to systematically select cytotoxic compounds. The system is innovative since it enables to derive a useful substance which uniquely suits a target gene from the DNA selective compounds (pyrrole-imidazole polyamides) of a countless combinations. The present inventors have already filed a patent application of the invention (JP-A-2001-136974).

The synthesis of pyrrole-imidazole polyamide has been conducted through the liquid phase method, but this method is not appropriate for the synthesis of a different type.

On the other hand, as a solid phase synthesis of a pyrrole-imidazole polyamide, the t-BOC method has been developed by Dr. Dervan of California Institute of Technology, U.S.A. (*J. Am. Chem. Soc.*, 1996, 118, 6141–6146); however, due to its strict reaction conditions, the method has a difficulty in synthesizing a long chain pyrrole-imidazole polyamide and is poor in applicability. Further, since the method does not use commercially available protein (peptide) synthesizers, it also has a difficulty in transferring a protein. Moreover, since the method has a difficulty in synthesizing a polyamide having a carboxyl group at its end and is poor in efficiency in excising the end from the solid phase as a carboxylic acid residue, it is difficult to impart a new reactivity to the obtained long chain pyrrole-imidazole polyamide by direct modification.

Further, though Fmoc synthesis method of polypyrrole has been reported by Dr. Mascarenas of Spain and Dr. Bruice of California University of U.S.A. (Tetrahedron Lett., 1999, 40, 3621–3624; J. Am. Chem. Soc., 2001, 123, 2469–2477), the polypyrrole cannot exactly distinguish DNA sequences because the imidazole amide is not transferred thereinto.

DISCLOSURE OF THE INVENTION

The present invention has been accomplished in view of the above-described circumstances, and an object of the invention is to provide a method of producing a pyrrole-imidazole polyamide, whereby a longer pyrrole-imidazole polyamide can be conveniently synthesized and a protein (peptide) can be easily transferred; the method enables to efficiently produce a pyrrole-imidazole polyamide having a carboxylic acid residue at its end which can be excised from a solid phase carrier, making it possible to directly transfer various functional groups thereinto, and capable of exactly distinguishing DNA sequences.

The present invention provides a pyrrole-imidazole polyamide synthesis method characterized by performing automatic synthesis by the solid phase Fmoc method with the use of a peptide synthesizer.

Also, the present invention provides a pyrrole-imidazole polyamide having a carboxyl group at its end.

Further, the present invention provides a pyrrole-imidazole polyamide obtainable by transferring a DNA alkylation agent into the carboxyl group at the end of the above pyrrole-imidazole polyamide.

Yet further, the present invention provides a sequence-specific DNA alkylation method characterized by using the above pyrrole-imidazole polyamide into which the DNA alkylation agent is transferred.

Furthermore, the present invention provides a FITC (fluorescein isothiocyanate)-pyrrole-imidazole polyamide conjugate having a carboxyl group at its end.

Specifically, the inventors have developed the automatic synthesis by the solid phase Fmoc method (Fmoc=9-fluorenylmethoxycarbonyl) as a method of conveniently synthesizing a longer pyrrole-imidazole polyamide. It is possible to quickly select a physiologically active pyrrole-imidazole polyamide from enormous combinations of pyrrole-imidazole polyamides by combining combinatorial automatic synthesis method by the solid phase Fmoc method and the above-described screening method developed by the inventors. Further, according to the method of the invention, since it is possible to excise the terminus from the solid phase carrier as a carboxylic acid residue, various functional groups can be transferred into the pyrrole-imidazole polyamide. For example, it is possible to transfer duocarmycin, pyrrolo-benzodiazepin, bleomycin enediyne compounds, nitrogen mustard, and their derivatives, all having the DNA alkylation ability. Also, since the method is the automatic synthesis using a commercially available protein (peptide) synthesizer, it is the synthesis method which enables a synthesis of a conjugate of a natural protein and a pyrrole-imidazole polyamide and a conjugate of a non-natural protein and a pyrrole-imidazole polyamide by automatic synthesis method. Moreover, since the reaction conditions of the Fmoc method are less strict than those of the t-BOC method, it is possible to transfer organic compounds, in addition to proteins, having a functional group which becomes unstable under the acidic condition and, therefore, the invention has a wider range of applicability. For example, it is possible to automatically synthesize conjugates of a pyrrole-imidazole polyamide and DNA, RNA, or a derivative thereof.

As described above, the conventional liquid phase method, for example, is not appropriate for synthesizing a different type, and the t-BOC method has a difficulty in synthesizing a long chain pyrrole-imidazole polyamide due to its strict reaction conditions as compared with those of the Fmoc method and is poor in applicability. Further, since the t-BOC method does not use any commercially available protein synthesizer, it also has a difficulty in transferring protein. Moreover, since the t-BOC method has a difficulty in excising the end from the solid phase as a carboxylic acid residue, it is difficult to impart a new reactivity to the obtained long chain pyrrole-imidazole polyamide by direct modification. The synthesis of polypyrrole by the Fmoc method also has a problem of failing to exactly distinguishing DNA sequences, which is caused because an imidazole is not transferred into a DNA with the method; however, the method developed by the present inventors is an innovative method which solves all of the above problems.

BEST MODE FOR CARRYING OUT THE INVENTION

Figure 1:
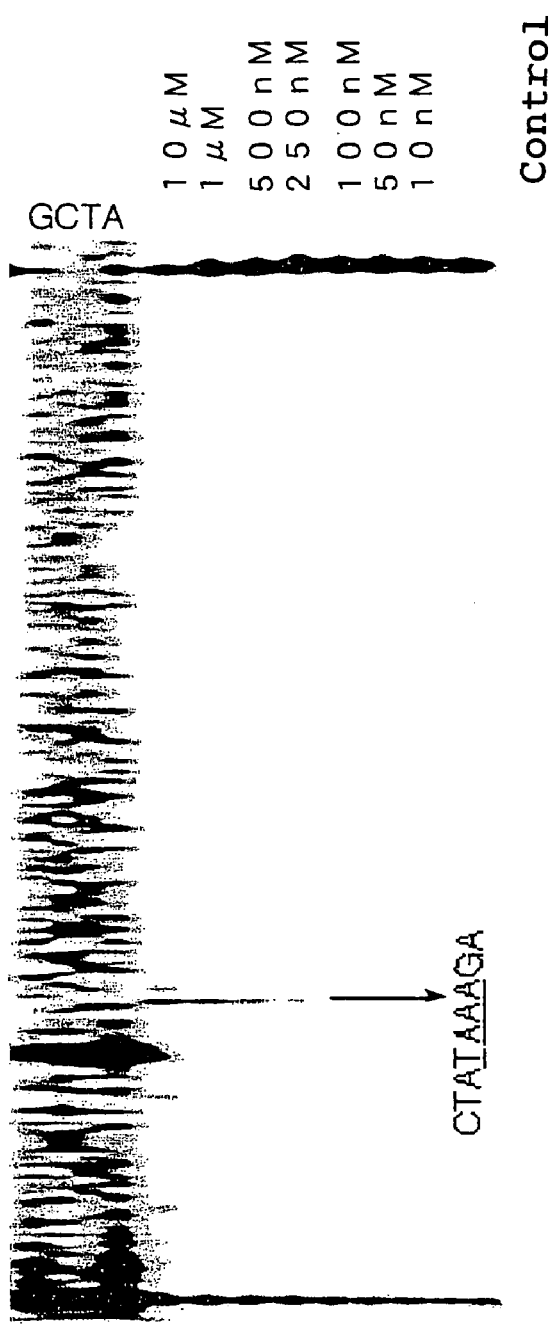
FIG. 1 shows a result of analyzing a reactivity of a DNA alkylation agent to a DNA by polyacrylamide gel electrophoresis using a DNA fragment of 450 mer in a DNA alkylation experiment of Example 4(1).

According to the synthesis method of the present invention, it is possible to conveniently and efficiently synthesize a pyrrole-imidazole polyamide having a carboxyl group at its end.

Specific examples of the pyrrole-imidazole polyamide having a carboxyl group at its end may be a pyrrole-imidazole polyamide having a β-alanine residue at its end, a pyrrole-imidazole polyamide having γ-aminobutyric acid residue at its end, and the like.

The pyrrole-imidazole polyamide having a β-alanine residue at its end or the pyrrole-imidazole polyamide having a γ-aminobutyric acid residue at its end may be synthesized by using an aminopyrrole carboxylic acid where the amino group is protected with Fmoc, an aminoimidazole carboxylic acid where the amino group is protected with Fmoc, and a solid phase carrier carrying β-alanine where the amino group is protected with Fmoc or γ-aminobutyric acid where the amino group is protected with Fmoc and by an automatic synthesis by the solid phase Fmoc method using a peptide synthesizer.

Specific examples of the aminopyrrole carboxylic acid may be 4-amino-2-pyrrole carboxylic acid, 4-amino-1-methyl-2-pyrrole carboxylic acid, 4-amino-1-ethyl-2-pyrrole carboxylic acid, 4-amino-1-propyl-2-pyrrole carboxylic acid, 4-amino-1-butyl-2-pyrrole carboxylic acid, and the like. Specific examples of the aminoimidazole carboxylic acid may be 4-amino-2-imidazole carboxylic acid, 4-amino-1-methyl-2-imidazole carboxylic acid, 4-amino-1-ethyl-2-imidazole carboxylic acid, 4-amino-1-propyl-2-imidazole carboxylic acid, 4-amino-1-butyl-2-imidazole carboxylic acid, and the like.

Reaction schemes of the syntheses of the aminopyrrole carboxylic acid where the amino group is protected with Fmoc and the aminoimidazole carboxylic acid where the amino group is protected with Fmoc in the case of using N-methylpyrrole or N-methylimidazole as a starting material by way of example are as follows. In addition, a reaction scheme of the synthesis of γ-aminobutyric acid where the amino group is protected with Fmoc is also shown below for reference.

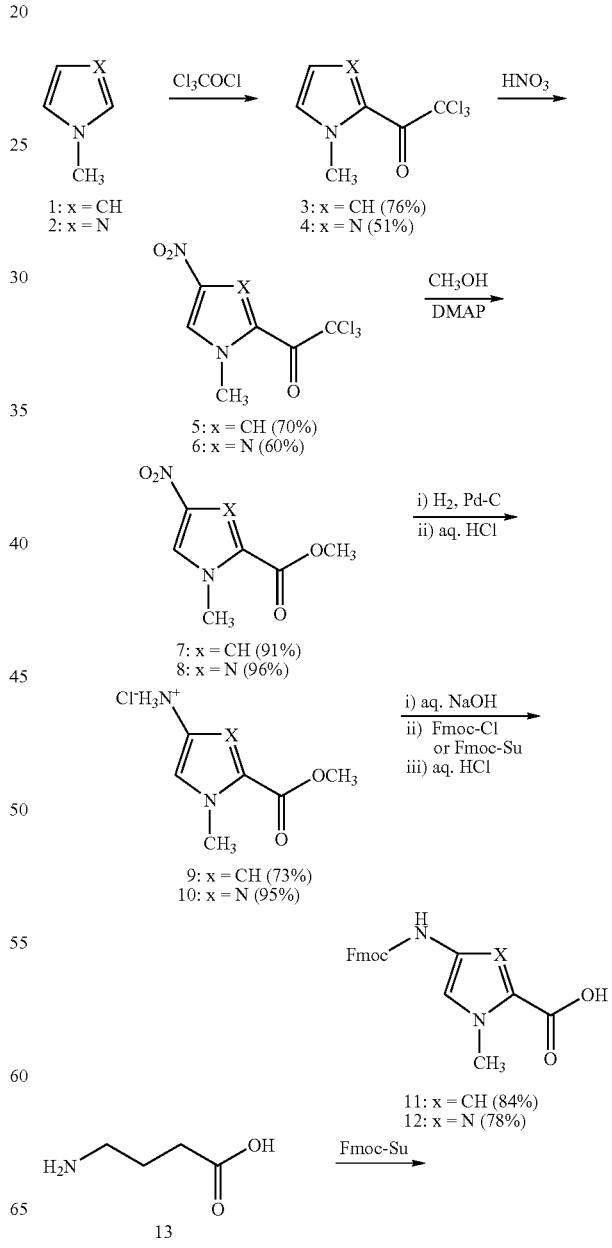

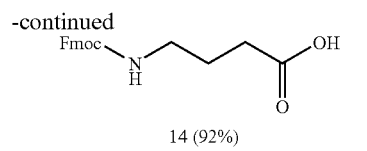

Details of the syntheses are described below in Examples.

The solid phase synthesis by the peptide synthesizer in the present invention is usually performed in a HATU[O-(7-azobenzotriazole-1-yl)-1,1,3,3-tetramethyluronium hexafluorophosphate]/DIEA (N,N-diisopropylethylamine) system.

Examples of the peptide synthesizer may be Pioneer (product of Applied Biosystems) which is a peptide synthesizer employing the Continuous Flow Method.

A reaction scheme of the solid phase synthesis of a pyrrole-imidazole polyamide of the present invention is as follows.

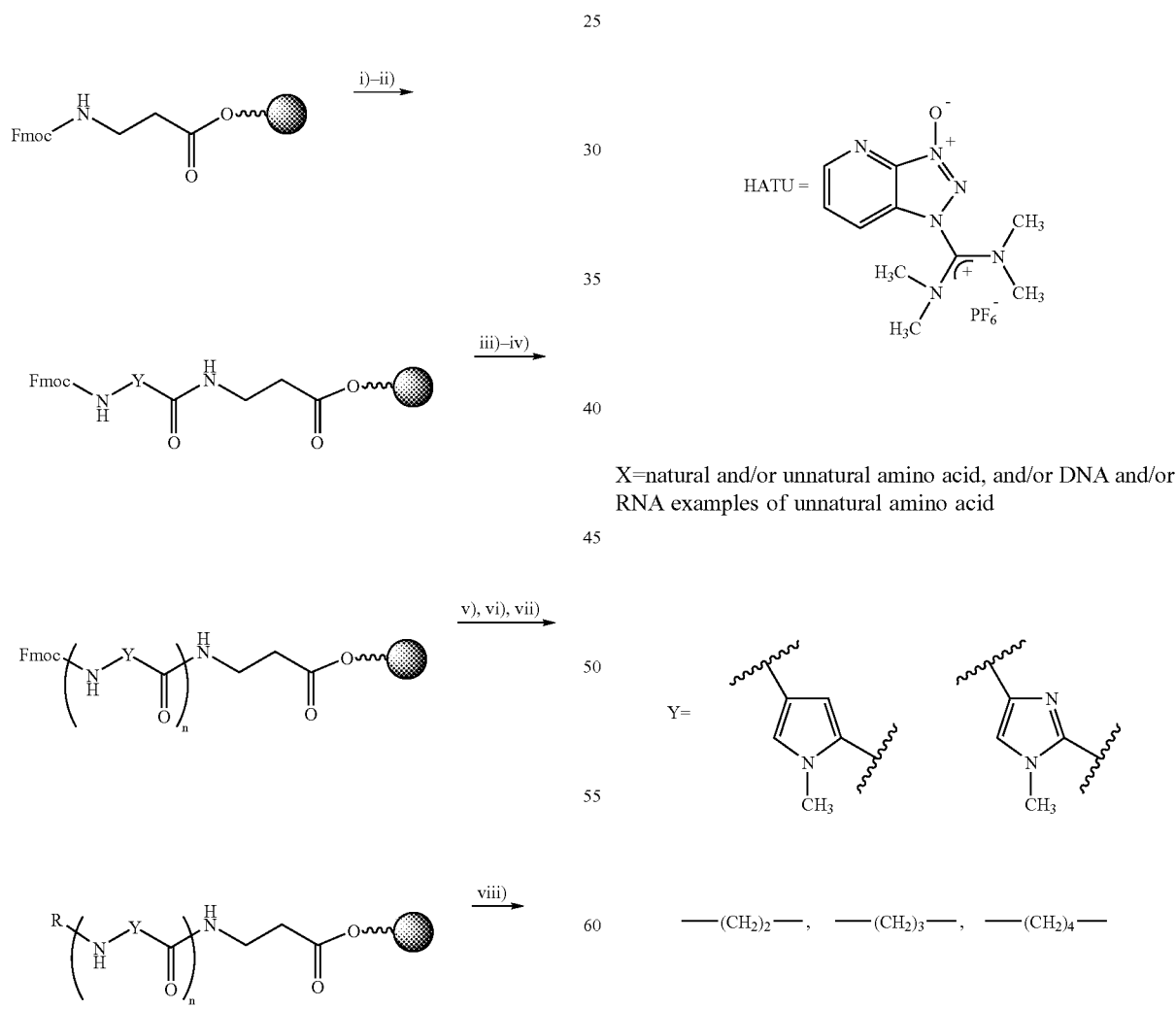

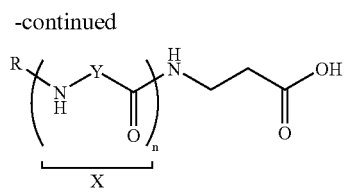

X=natural and/or unnatural amino acid, and/or DNA and/or RNA examples of unnatural amino acid i) 20% piperidine/DMF solution; ii) monomer unit, HATU/DIEA; iii) 20% piperidine/DMF solution; iv) monomer unit, HATU/DIEA; v) 20% piperidine/DMF solution; vi) 5% acetic anhydride, 5% pyridine/DMF solution; vii) collection, drying under reduced pressure; viii) 95% TFA (trifluoroacetic acid), 2.5% TIS (triisopropylsilane), 2.5% water.

Details of the synthesis are described later in Examples.

According to the method of the present invention, it is possible to transfer various functional groups into a pyrrole-imidazole polyamide because its end can be excised from the solid phase carrier as a carboxylic acid residue. The case of transfer of a DNA alkylation agent is described below by way of example.

For example, an A-ring (Du86) which is an active center of the DNA alkylation agent: DU-86 (2-methyl-3-methoxycarbonyl-A ring pyrrole-DUMA), is transferred into the carboxylic acid end excised from the solid phase carrier as follows. A pyrrole-imidazole polyamide having a carboxylic acid end is dissolved into a solvent such as DMF, and then carbonyldiimidazole (CDI) is added to the mixture under a room temperature to be stirred overnight at the same temperature. After that, the solvent is distilled under a reduced pressure, and then the residue is washed with diethylether or the like to obtain an imidazole ester substance.

Du86 is dissolved into a solvent such as DMF, and then sodium hydride is added to the mixture under cooling (at −15° C., for example), followed by stirring for 30 minutes. A DMF solution containing the imidazole ester obtained above is dropped into the mixture, followed by stirring overnight at the same temperature. After adding a sodium phosphate buffer (pH6.86) or the like to the mixture to adjust pH, the solvent is distilled under a reduced pressure. The obtained residue is purified by silica gel column chromatography and HPLC or the like to obtain a coupling substance (a pyrrole-imidazole polyamide into which the DNA alkylation agent is transferred).

A sequence-specific DNA alkylation becomes possible by the use of the thus-obtained pyrrole-imidazole polyamide into which the DNA alkylation agent is transferred.

Details of the synthesis are described below in Examples.

FITC (fluorescein isothiocyanate) has been known as a fluorescent labeling reagent for antibodies from a long time ago. As a further development of the pyrrole-imidazole polyamide synthesis by the Fmoc method, which has been developed by the inventors, it is possible to synthesize a conjugate by transferring FITC into the pyrrole-imidazole polyamide. The conjugate to be obtained is usable as a fluorescent labeling reagent which recognizes a specific DNA sequence and is capable of readily distinguishing DNA sequences relating to genetic diseases such as cancer. Such conjugate can be used not only in a stage preceding a treatment with the pyrrole-imidazole polyamide, but also as a diagnostic drug.

The synthesis of the conjugate can be performed in the same manner as in the above-described solid phase synthesis of the pyrrole-imidazole polyamide, i.e., by the automatic synthesis by the solid phase Fmoc method with the use of the peptide synthesizer employing the Continuous Flow Method, such as Pioneer available from Applied Biosystems.

Details of the synthesis are described below in Examples.

EXAMPLES

Hereinafter, the present invention will be described in more details according to examples, but the invention is not limited by the examples at all.

Example 1

Synthesis of Monomer Units (See the Reaction Scheme of [Chem. 1])

Monomer units 11, 12, and 14 to be used for the solid phase synthesis were synthesized by the following processes. A commercially available protector was used as a Fmoc protector for β-alanine.

Commercially available reagents and solvents were used for the following reactions and purifications. Used as $^1$H-NMR was JNM-A500 available from Japan Electron Optics Laboratory, Co.

Abbreviations for the reagents are as follows: dimethylformamide (DMF); diisopropylethylamine (DIEA); triisopropylsilane (TIS); trifluoroacetic acid (TFA); carbonyldiimidazole (CDI); and 4-dimethylaminopyridine (DMAP).

(1) Synthesis of 1-methyl-2-trichloroacetylpyrrole (3)

A methylene chloride solution (200 ml) containing 1 (90.3 g, 1.10 mol) was added to a methylene chloride solution (600 ml) containing trichloroacetylchloride (200.0 g, 1.10 mol) by 3 hours' dripping. During the dripping, a nitrogen gas was sprayed so as to eliminate hydrogen chloride which is generated during the reaction. After stirring the mixture overnight, the solvent was distilled under a reduced pressure. The residue was subjected to silica gel column chromatography to obtain a trichloroacetyl substance 3 (189.7 g, 76%) from an elution position of ethyl acetate-hexane (1:10, v/v).

$^1$H-NMR (CDCl$_3$)δ: 3.95 (3H, s), 6.20 (1H, s), 6.95 (1H, s), 7.48 (1H, s); $^{13}$C-NMR (CDCl$_3$)δ: 38.5, 96.3, 108.9, 121.8, 124.0, 133.6, 172.9; IR (KBr) ν: 1657, 1404, 1363, 1334, 1102, 1069, 845, 808, 745, 690 cm$^{-1}$.

(2) Synthesis of 1-methyl-4-nitro-2-trichloroacetylpyrrole (5)

An acetic anhydride solution (200 ml) containing 3 (45.2 g, 0.200 mol) was cooled to −40° C., and then fuming nitric acid (18.5 ml, 0.360 mol) was dropped into the solution at the same temperature. After stirring the mixture for 2 hours at a room temperature, isopropanol was added to precipitate a solid. The precipitated solid was collected by filtration to obtain a nitro substance 5 (27.2 g). The filtrate was distilled under a reduced pressure, and the obtained residue was subjected to silica gel column chromatography to further obtain 5 (10.7 g) from an elusion position of ethyl acetate-hexane (1:10, v/v). (Total yield: 70%)

$^1$H-NMR (CDCl$_3$)δ: 4.06(3H, s), 7.72(1H, s), 7.93(1H, s); $^{13}$C-NMR (CDCl$_3$)δ: 39.7, 94.8, 117.5, 121.4, 130.2, 135.3, 173.6; IR (KBr) ν: 1698, 1406, 1325, 1226, 1185, 1112, 998, 857, 810, 752, 716, 683 cm$^{-1}$.

(3) Synthesis of 1-methyl-4-nitro-2-trichloroacetylimidazole (6)

A methylene chloride solution (80 ml) containing 2 (16.4 g, 0.20 mol) was added to a methylene chloride solution (120 ml) containing trichloroacetylchloride (36.3 g, 0.20 mol) by 2 hours' dripping. After stirring the mixture for 4 hours, triethylamine (20.2 g, 0.20 mol) was dropped thereinto at an ice cool temperature. After distilling the solvent under a reduced pressure, the residue was subjected to silica gel column chromatography to obtain a trichloroacetyl substance 4 (23.2 g, 51%) from an elution position of ethyl acetate-hexane (1:1, v/v).

$^1$H-NMR (CDCl$_3$)δ: 4.03 (3H, s), 7.14 (1H, s), 7.32 (1H, s); $^{13}$C-NMR (CDCl$_3$)δ: 37.1, 94.8, 128.5, 130.5, 136.1, 172.3; IR (KBr)ν: 1657, 1518, 1466, 1408, 1352, 1313, 1278, 810, 779 cm$^{-1}$

An acetic anhydride solution (200 ml) was cooled to an ice cool temperature, and then fuming nitric acid (18.5 ml, 0.360 mol) was added to the solution at the same temperature. Concentrated sulphuric acid (0.5 ml) was added to the mixture at the same temperature, and then 4 (34.0 g, 0.150 mol) was added by a small amount for 2 hours, followed by stirring the mixture overnight. The solvent was distilled under a reduced pressure, and the obtained residue was washed with chloroform to obtain 6 (16.0 g). The same operation was repeated twice to further obtain 6 (8.6 g). (Total yield: 60%)

$^1$H-NMR (CDCl$_3$)δ: 4.10(3H, s), 7.90(1H, s); $^{13}$C-NMR (CDCl$_3$)δ: 38.2, 93.5, 126.0, 133.6, 145.8, 172.8; IR (KBr) ν: 1709, 1541, 1514, 1491, 1464, 1344, 1317, 1135, 1023, 1000, 816, 743, 638 cm$^{-1}$ (4) Synthesis of methyl 4-nitro-1-methylpyrrole-2-carboxylic acid ester (7)

After adding DMAP (0.50 g, 4.55 mmol) to a methanol solution (140 ml) containing 5 (32.4 g, 0.12 mol), the mixture was stirred for 40 minutes. After that, precipitates were collected by filtration and then washed with methanol to obtain 7 (18.9 g). After distilling the filtrate under a reduced pressure, the same operation was repeated to further obtain 7 (2.3 g). (Total yield: 97%)

$^1$H-NMR (CDCl$_3$)δ: 3.84(3H, s), 3.97(3H, s), 7.39(1H, d, J=2.0 Hz), 7.57(1H, d, J=2.0 Hz); IR (KBr) ν: 1711, 1541, 1510, 1425, 1315, 1257, 1195, 1118, 1089, 752 cm$^{-1}$.

(5) Synthesis of methyl 4-nitro-1-methylimidazole-2-carboxilic acid ester (8)

After adding DMAP (0.500 g, 4.55 mmol) to a methanol solution (500 ml) containing 6 (70.0 g, 256 mmol), the mixture was stirred for 2 hours. After that, precipitates were collected by filtration and then washed with diethylether to obtain 8. After distilling the filtrate under a reduced pressure, the same operation was repeated twice to obtain 8. (46.0 g, 97%)

$^1$H-NMR (CDCl$_3$)δ: 3.96 (3H, s), 4.10 (3H, s), 7.82 (1H, s); $^{13}$C-NMR (CDCl$_3$)δ: 37.0, 52.8, 124.2, 134.6, 145.8, 158.4; IR (KBr)ν: 1729, 1643, 1497, 1460, 1377, 1350, 1313, 1265, 1147, 1129, 998, 845, 814, 656 cm$^{-1}$ (6) Synthesis of 1-methyl-4-aminopyrrole-2-carboxylic acid methyl ester hydrochloride (9)

After dissolving 7 (15.3 g, 83.0 mmol) into a mixed solution of methanol and dichloromethane (150 ml, 1:2, v/v), 10% palladium carbon (3 g) was added to the mixture to be suspended, followed by stirring the suspension for 2 days under a hydrogen atmosphere. After that, the suspension was filtered through a celite to remove palladium carbon, and 10% hydrochloric acid was added to the filtrate. Precipitates thus generated were collected by filtration to obtain 9 (4.71 g). After distilling the filtrate under a reduced pressure, recrystallization was performed by using acetate ethyl-methanol to further obtain 9 (6.86 g). (Total yield 11.6 g, 73%)

$^1$H-NMR (DMSO-d$_6$)δ: 3.74(3H, s), 3.85(3H, s), 6.80 (1H, s), 7.25(1H, s), 10.07(3H, br); ESI MS: m/e calcd for C$_7$H$_{10}$N$_2$O$_2$ (M−HCl+H) 154.1, found 154.1

(7) Synthesis of 1-methyl-4-aminoimidazole-2-carboxylic acid methyl ester hydrochloride (10)

10% palladium carbon (5 g) was added to a dichloromethane solution (300 ml) containing 8 (20.0 g, 108 mmol) to suspend the solution, followed by stirring the suspension for a day under a hydrogen atmosphere. After that, the suspension was filtered through a celite to remove palladium carbon, and then 10% hydrochloric acid was added to acidify the filtrate. Precipitates were collected by filtration to obtain 10 (19.8 g, 96%).

$^1$H-NMR (DMSO-d$_6$)δ: 3.83(3H, s), 3.93(3H, s), 7.37 (1H, s), 9.96(3H, br.s); ESI MS: m/e calcd for C$_6$H$_9$N$_3$O$_2$ (M−HCl+H) 156.1, found 156.1

(8) Synthesis of 4-[(9-fluorenylmethoxycarbonyl)amino]-1-methyl-2-pyrrole carboxylic acid (11)

After dissolving 9 (10.9 g, 57.2 mmol) into distilled water (80 ml), sodium hydroxide (9.2 g) was added to the solution. After stirring overnight, the solution was neutralized with 1N hydrochloric acid, followed by distillation under a reduced pressure. The residue was dissolved into a mixed solution of water and ethyleneglycoldimethylether (100 ml, 1:1, v/v) to be used for next reaction. After dissolving sodium carbonate (5.3 g) into the solution, 9-fluorenylmethylchloroformate (17.8 g, 68.6 mmol) was added thereto. After stirring the mixture overnight, precipitates were collected by filtration to obtain 11 (12.3 g, 34.1 mmol). The filtrate was added to a mixed solution of 1M sodium carbonate solution and diethylether (1:1, v/v). Precipitates were collected by filtration to further obtain 11 (3.4 g). After acidifying the water layer with 10% hydrochloric acid, the water layer was extracted with ethyl acetate. The organic layer was distilled under a reduced pressure and then recrystallized with hexane-dioxane to further obtain 11 (1.6 g). (Total yield: 17.3 g, 84%)

$^1$H-NMR (DMSO-d$_6$)δ: 3.77 (3H, s), 4.27 (1H, t, J=6.0 Hz), 4.43 (2H, d, J=6.0 Hz), 6.60 (1H, s), 7.02 (1H, s), 7.32 (2H, t, J=7.5 Hz), 7.41 (2H, t, J=7.5 Hz), 7.70 (2H, d, J=7.5 Hz), 7.89 (2H, d, J=7.5 Hz), 9.40 (1H, s); $^{13}$C-NMR (DMSO-d$_6$) δ: 36.1, 46.7, 65.4, 107.6, 118.8, 119.9, 120.1, 122.4, 125.0, 127.1, 127.6, 140.8, 143.8, 153.3, 161.8

(9) Synthesis of 4-[(9-florenylmethoxycarbonyl)amino]-1-methyl-2-imidazole carboxylic acid (12)

After dissolving 10 (8.24 g, 41.9 mmol) into distilled water (60 ml), sodium hydroxide (4.2 g) was added to the solution. After stirring overnight, the solution was neutralized with 1N hydrochloric acid, followed by distillation under a reduced pressure. The residue was dissolved into a mixed solution of water and ethyleneglycoldimethylether (200 ml, 1:1, v/v) to be used for the next reaction. After dissolving sodium hydrogen carbonate (14.1 g) into the solution, 9-fluorenylmethylsuccinimidyl carbonate (16.9 g, 50.1 mmol) was added thereto. After stirring the mixture overnight, precipitates were collected by filtration to obtain 12 (10.8 g, 29.7 mmol). After acidifying the filtrate with 10% hydrochloric acid, precipitates thus generated were collected by filtration and washed with ethyl acetate to further obtain 12 (1.2 g, 3.30 mmol). (Total yield: 12.0 g, 79%)

$^1$H-NMR (DMSO-d$_6$)δ: 3.87(3H, s), 4.27(1H, t, J=6.0 Hz), 4.51(2H, d, J=6.0 Hz), 6.80(1H, s), 7.32(2H, t, J=7.5 Hz), 7.41(2H, t, J=7.5 Hz), 7.70(2H, d, J=7.5 Hz), 7.89 (2H, d, J=7.5 Hz), 9.50(1H, s); $^{13}$C-NMR (DMSO-d$_6$)δ: 35.4, 46.5, 66.1, 113.4, 120.1, 125.4, 127.1, 127.7, 132.04, 137.4, 140.7, 143.7, 153.3, 159.9;

MS spectrum was measured after the conversion into methylester. HRMS (EI+): m/e calcd for C$_{21}$H$_{19}$N$_3$O$_4$ (M) as methyl ester 377.1376, found 377.1380.

(10) Synthesis of 4-(9-fluorenylmethoxycarbonyl)aminobutyric acid (14)

After dissolving 13 (5.0 g, 48.5 mmol) into a mixed solution of water and ethyleneglycoldimethylether (200 ml, 1:1, v/v), 9-fluorenylmethylsuccinimidyl carbonate (16.4 g, 48.6 mmol) was added to the mixture. After adding sodium carbonate (10 g, 94.4 mmol), the mixture was stirred overnight. The generated precipitates were collected by filtration to obtain 14 (10.3 g). After acidifying the filtrate with 1N hydrochloric acid, the generated precipitates were collected by filtration to further obtain 14 (4.4 g). (Total yield: 14.7 g, 94%)

$^1$H-NMR (DMSO-$d_6$)δ: 1.61 (2H, t, J=7.0 Hz), 2.19 (2H, t, J=7.0 Hz), 2.98, (2H, dd, J=13.0, 6.0 Hz), 4.20 (1H, t, J=6.5 Hz), 4.28 (2H, d, J=6.5 Hz), 7.32 (2H, t, J=7.5 Hz), 7.40 (2H, t, J=7.5 Hz), 7.67 (2H, d, J=7.5 Hz), 7.87 (2H, d, J=7.5 Hz), 11.0 (1H, br.s);

MS spectrum was measured after the conversion into methylester. HRMS (EI+): m/e calcd for $C_{19}H_{19}NO_4$ as methyl ester 339.1471, found 339.1475.

Example 2

Solid Phase Synthesis of Pyrrole-Imidazole Polyamide (See the Reaction Scheme of [Chem. 2])

Syntheses of various pyrrole-imidazole polyamides were conducted by using the compounds 11, 12, 14 obtained in Example 1 and a commercially available Fmoc protector for β-alanine. The synthesis protocol is shown in Table 1.

TABLE 1

| | Synthesis Step | Time |
|---|---|---|
| 1, deprotection | 20% piperidine/DMF | 5 minutes |
| 2, washing | methanol | 50 seconds |
| 3, condensation | HATU/DIEA | 60 minutes |
| 4, washing | methanol | 40 seconds |
| 5, protection | acetic anhydride/pyridine | 10 minutes |
| 6, excision | 95% TFA, 2.5% TIS, 2.5% water | 30 minutes |

The solid phase synthesis is performed by using Pioneer (product of Applied Biosystems), which is a peptide synthesizer employing the Continuous Flow Method. Used as a solid phase carrier was a commercially available Wang resin to which Fmoc-β-alanine is preloaded. Four equivalent amounts of each of HATU, DIEA and the monomer units are used with respect to an active end of the solid phase carrier.

In advance of the synthesis, the solid phase carrier was swelled with DMF for 30 minutes, and then filled in a synthesis column of Pioneer. First, the Fmoc group of β-alanine preloaded to the carrier was deprotected by 5 minutes of treatment with the DMF solution containing 20% piperidine. After that, the carrier was washed with methanol for 50 seconds, and then the monomer unit, HATU, and DIEA to be transferred were passed through the column to be subjected to a cycling for 60 minutes, followed by washing again with methanol for 40 seconds. The deprotection and the elongation were counted as one cycle, and the monomer units were condensed in accordance with the order of a sequence of a target polyamide. After that, the deprotection was performed in the same manner, and an acetylation was performed by using the DMF solution containing 5% acetic anhydride and 5% pyridine. After termination of the reaction, the solid phase carrier was taken out from the column to be subjected to a drying under reduced pressure and then moved to a 50 ml curved flask. 5 ml of the solution containing 95% TFA, 2.5% TIS, and 2.5% water was added to the solid phase carrier to be stirred for 30 minutes, whereby excising the polyamide from the carrier. Purification was performed by HPLC using a 0.1% TFA solution and acetonitrile.

Structural formulas, yields, and various spectrum data of the obtained pyrrole-imidazole polyamides are as shown below.

In addition, Im represents a 1-methyl-4-aminoimidazole-2-carboxylic acid residue; Py represents a 1-methyl-4-aminopyrrole-2-carboxylic acid residue; Ac represents an acetyl group; γ-butyl represents a γ-aminobutyric acid residue; and β-ala-COOH represents β-alanine in the following description.

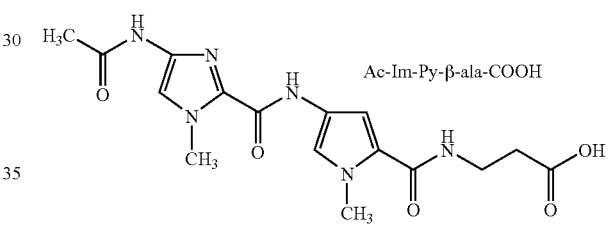

Ac-Im-β-ala-COOH: yield 19%; $^1$H NMR (CD$_3$OD)δ: 2.15 (3H, s), 2.63 (2H, t, J=6.5 Hz), 3.60 (2H, t, J=6.5 Hz), 3.90 (3H, s), 4.04 (3H, s), 6.71 (1H, d, J=1.5 Hz), 7.24 (1H, d, J=1.5 Hz), 7.35 (1H, s), Four protons (3 N<u>H</u>s and 1 COO<u>H</u>) were not detected due to the conversion into CD$_3$OD. ESI MS m/e calcd. for $C_{16}H_{21}O_5N_6$ (M+H) 377.2, found 377.2.

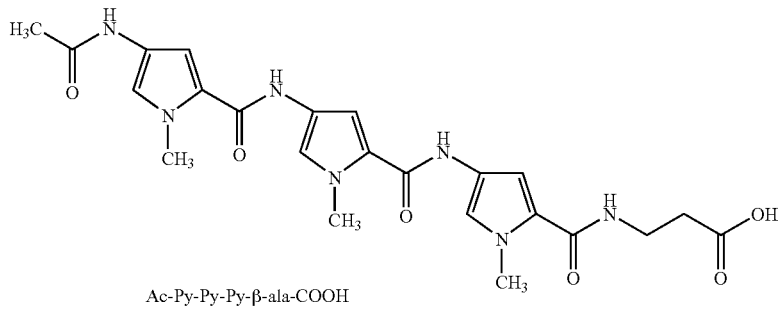

Ac-Py-Py-Py-β-ala-COOH

Ac-Py-Py-Py-β-ala-COOH: yield 18%; $^1$H NMR (CD$_3$OD)δ: 2.07 (3H, s), 2.60 (2H, t, J=7.0 Hz), 3.55 (2H, t, J=7.0 Hz), 3.87 (3H, s), 3.89 (3H, s), 3.90 (3H, s), 6.76 (1H, s), 6.82 (1H, s), 6.91 (1H, s), 7.11 (3H, s), 7.18 (2H, s), Five protons (4 N<u>H</u>s and 1 COO<u>H</u>) were not detected due to the conversion into CD$_3$OD. ESI MS m/e calcd. for $C_{23}H_{28}O_6N_7$ (M+H) 498.2, found 498.3.

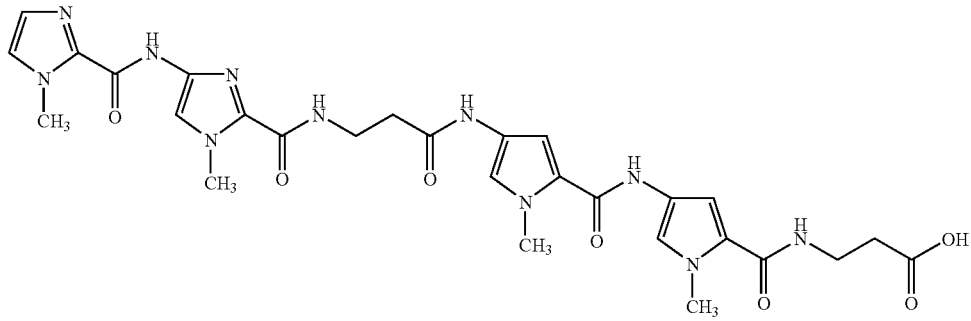

Im-Im-β-ala-Py-Py-β-ala-COOH

Im-Im-β-ala-Py-Py-β-ala-COOH: yield 31%; $^1$H NMR (CD$_3$OD) δ: 2.59 (2H, t, J=7.0 Hz), 2.62 (2H, t, J=7.0 Hz), 3.54 (2H, t, J=7.0 Hz), 3.67 (2H, t, J=7.0 Hz), 3.83 (3H, s), 3.86 (3H, s), 4.01 (3H, s), 4.11 (3H, s), 6.74 (1H, d, J=2.0 Hz), 6.79 (1H, d, J=2.0 Hz), 7.13 (1H, d, J=2.0 Hz), 7.14 (1H, d, J=2.0 Hz), 7.51 (1H, s), 7.54 (1H, s), 7.62 (1H, s), Six protons (5 NHs and 1 COOH) were not detected due to the conversion into CD$_3$OD. ESI MS m/e calcd. for C$_{29}$H$_{34}$O$_7$N$_{11}$ (M+H) 636.3, found 636.3.

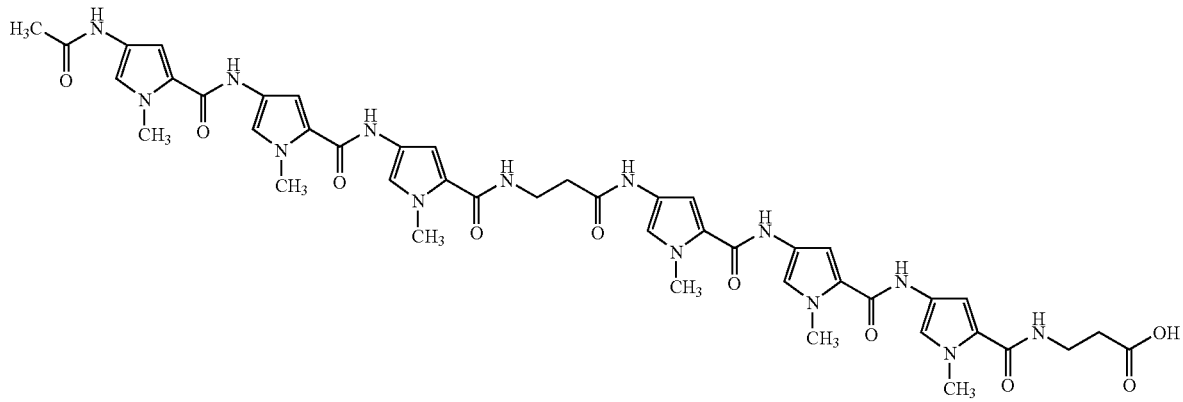

Ac-Py-Py-Py-β-ala-Py-Py-Py-β-ala-COOH

Ac-Py-Py-Py-β-ala-Py-Py-Py-β-ala-COOH: yield 18%; $^1$H NMR (CD$_3$OD) δ: 2.06 (3H, s), 2.59 (2H, t, J=7.0 Hz), 2.62 (2H, t, J=7.0 Hz), 3.55 (2H, t, J=7.0 Hz), 3.63 (2H, t, J=7.0 Hz), 3.85 (3H, s), 3.86 (6H, s), 3.87 (3H, s), 3.88 (3H, s), 3.89 (3H, s), 6.75 (1H, d, J=2.0 Hz), 6.76 (1H, d, J=2.0 Hz), 6.81 (1H, d, J=2.0 Hz), 6.83 (1H, d, J=2.0 Hz), 6.88 (1H, d, J=2.0 Hz), 6.89 (1H, d, J=2.0 Hz), 7.11 (1H, d, J=2.0 Hz), 7.14–7.16 (4H, m), 7.17 (1H, d, J=2.0 Hz), Nine protons (8 NHs and 1 COOH) were not detected due to the conversion into CD$_3$OD. ESI MS m/e calcd. for C$_{44}$H$_{51}$O$_{10}$N$_{14}$ (M+H) 935.4, found 935.4.

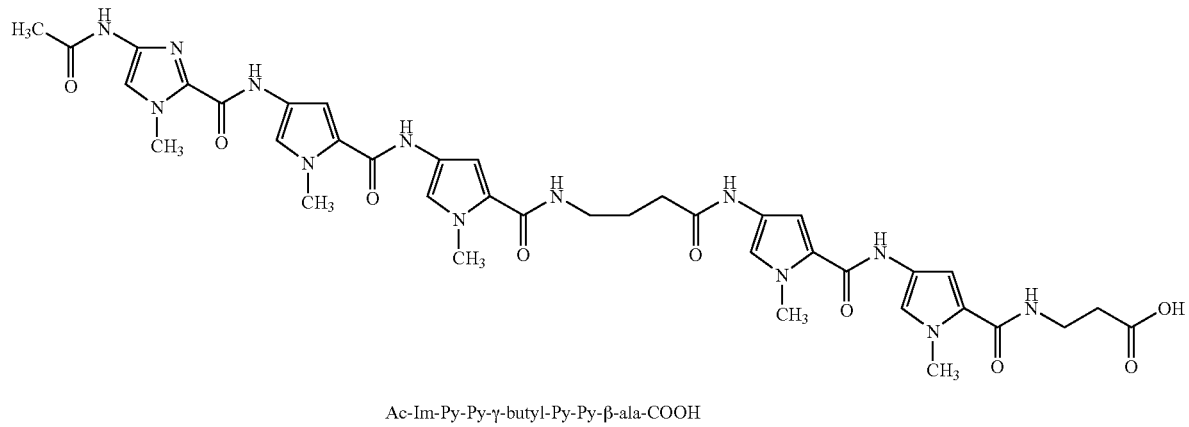

Ac-Im-Py-Py-γ-butyl-Py-Py-β-ala-COOH

Ac-Im-Py-Py-γ-butyl-Py-Py-β-ala-COOH: yield 18%; $^1$H NMR (CD$_3$OD)δ: 1.78(2H, t, J=7.5 Hz), 2.01(3H, s), 2.27 (2H, t, J=7.5 Hz), 3.21(2H, dd, J=7.5, 12.5 Hz), 3.79(3H, s), 3.80(3H, s), 3.82(3H, s), 3.83(3H, s), 3.84(3H, s), 3.94(3H, s), 6.84(1H, d, J=1.5), 6.86(1H, d, J=1.5), 6.89(1H, d, J=1.5), 7.02(1H, d, J=1.5), 7.12(1H, d, J=1.5), 7.16–7.17 (3H, m), 7.22(1H, d, J=1.5), 7.26(1H, d, J=1.5), 7.41 (1H, s), 7.99(1H, t, J=6.5), 8.03(1H, t, J=6.5), 9.81 (1H, s), 9.87(1H, s), 9.88(2H, s), 9.93(1H, s), 10.21 (1H, s), Three protons (N—CH2-CH2-COO, and COOH) were not detected. (due to the overlapping) ESI MS m/e calcd. for C$_{38}$H$_{48}$O$_{13}$N$_9$ (M+H) 828.3, found 828.3.

not confirmed due to the overlap with one of the peaks of the DMSO solvent. ESI MS m/e calcd. for C$_{44}$H$_{53}$O$_{10}$N$_{15}$ (M+H) 950.4, found 950.3.

Example 3

Transfer of DNA Alkylation Agent into Carboxylic Acid End of Pyrrole-Imidazole Polyamide Structural formulas of DU-86 which is the DNA alkylation agent and the A ring (Du86) which is the active center of DU-86 are shown below.

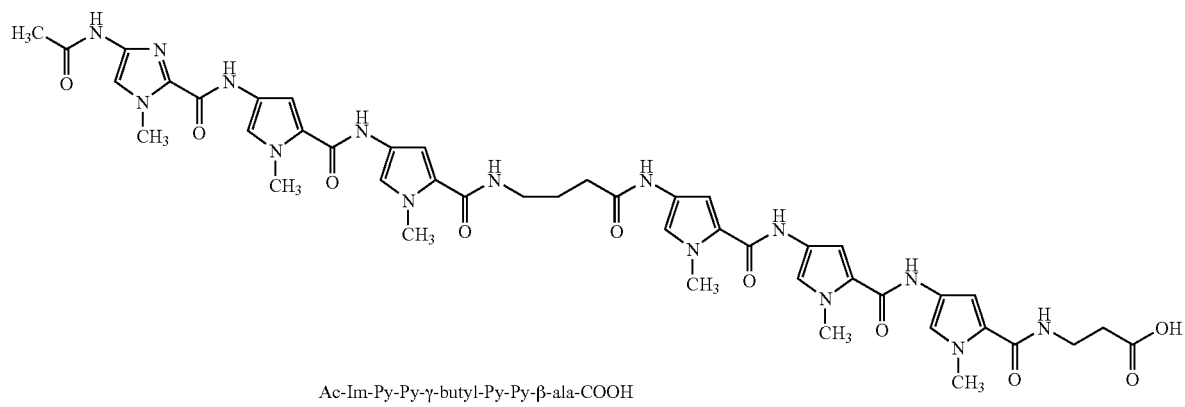

Ac-Im-Py-Py-γ-butyl-Py-Py-Py-β-ala-COOH

Ac-Im-Py-Py-γ-butyl-Py-Py-Py-β-ala-COOH: yield 10%; $^1$H NMR (DMSO-d$_6$)δ: 1.78 (2H, t, J=7.5 Hz), 2.01 (3H, s), 2.27 (2H, t, J=7.5 Hz), 3.21 (2H, dd, J=12.5, 7.5 Hz), 3.79 (3H, s), 3.80 (6H, s), 3.82 (3H, s), 3.83 (3H, s), 3.85 (3H, s), 3.94 (3H, s), 6.84 (1H, d, J=2.0 Hz), 6.86 (1H, d, J=2.0 Hz), 6.89 (1H, d, J=2.0 Hz), 7.02 (1H, d, J=2.0 Hz), 7.12 (1H, d, J=2.0 Hz), 7.16–7.17 (2H, m), 7.22 (1H, d, J=2.0 Hz), 7.26 (1H, d, J=2.0 Hz), 7.99 (1H, t, J=6.0 Hz), 8.03 (1H, t, J=6.0 Hz), 9.81 (1H, s), 9.87 (2H, s), 9.88 (2H, s), 9.93 (1H, s), 10.21 (1H, s), Four protons (N—CH$_2$—CH$_2$—COOH) were

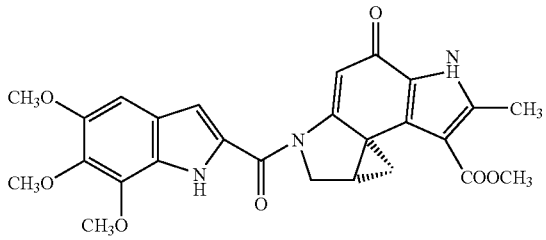

2-methyl-3-methoxycarbonyl-A ring pyrrole-DUMA (DU-86)

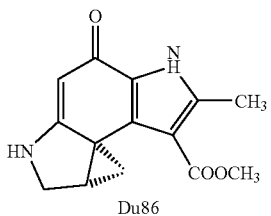

(15)

Du86

The A ring (Du86) 15 which is the active center of DU-86 of the is the DNA alkylation agent is transferred into the carboxylic acid end excised from the solid phase carrier. The operating procedure is as described below.

Carbonyldiimidazole (CDI, 24.3 mg, 0.15 mmol) was added to a DMF solution (1.5 mL) containing the pyrrole-imidazole polyamide (0.05 mmol) having the carboxylic acid end obtained in Example 2 under a room temperature, followed by stirring the mixture overnight. The solvent was distilled under a reduced pressure, and the residue was washed twice with diethylether to obtain an imidazole ester substance (30 to 70%).

A DMF solution (2 mL) containing 15 (6.2 mg, 0.024 mmol) was cooled to −15° C., followed by an addition of 60% sodium hydride (2.0 mg, 0.05 mmol), and then the mixture was stirred for 30 minutes at the same temperature. After dropping a DMF solution (1.5 mL) containing the imidazole ester obtained above (0.024 mmol), the mixture was stirred overnight at the same temperature. After adding sodium phosphate buffer (pH 6.86) to the mixture, the solvent was distilled under a reduced pressure. The obtained residue was subjected to silica gel column chromatography, followed by a purification by HPLC to obtain a coupling substance (20 to 50%).

Structural formulas, obtained amounts, yields, and various spectrum data of the thus-obtained imidazole-ester substances and the coupling substances are shown below.

In addition, in the following description, Im' represents an imidazolyl group; β-ala-CO represents a β-alanine residue; Ac, Im, Py, and γ-butyl are the same as described above.

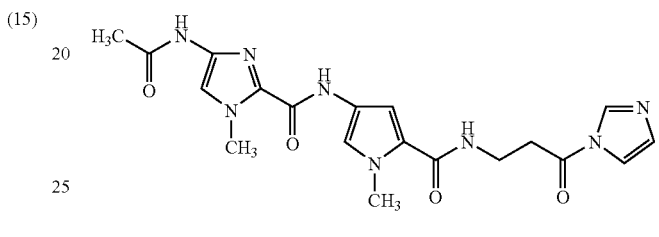

Ac-Im-Py-β-ala-CO-Im': 5.6 mg (45%); $^1$H NMR (DMSO-$d_6$) δ: 2.01(3H, s), 3.78 (3H, s), 3.92 (3H, s), 6.93 (1H, d, J=1.5 Hz), 7.06 (1H, s), 7.21 (1H, d, J=1.5 Hz), 7.40 (1H, s), 7.72 (1H, s), 8.14 (1H, t, J=5.5 Hz), 8.42 (1H, s), 9.92 (1H, s), 10.23 (1H, s), Four protons (N—C$\underline{H}_2$—C$\underline{H}_2$—COO) were not confirmed due to the overlap with the peak of the DMSO solvent. ESI MS m/e calcd. for $C_{19}H_{23}O_4N_8$ (M+H) 427.2, found 427.2.

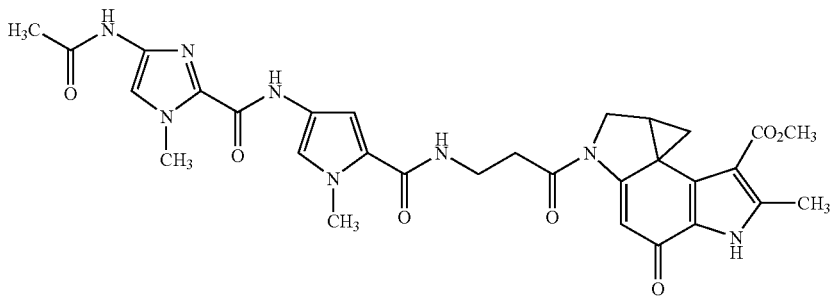

Ac-Im-Py-β-ala-CO-Du86: 0.56 mg (9%); $^1$H NMR (DMSO-$d_6$)δ: 1.28 (1H, s), 2.01 (3H, s), 2.09 (1H, s), 2.45 (3H, s), 3.38–3.44 (2H, m), 3.70–3.75 (1H, m), 3.71 (3H, s), 3.80 (3H, s), 3.92 (3H, s), 4.08 (2H, s), 6.93 (2H, s), 7.22 (1H, s), 7.40 (1H, s), 8.03 (1H, t, J=5.5 Hz), 9.89 (1H, s), 10.22 (1H, s), 12.35 (1H, s), Two protons (N—C$\underline{H}_2$—C$\underline{H}_2$—COO) were not confirmed due to the overlap with one of the peaks of the DMSO solvent. ESI MS m/e calcd. for $C_{30}H_{33}O_7N_3$ (M+H) 617.2, found 617.3.

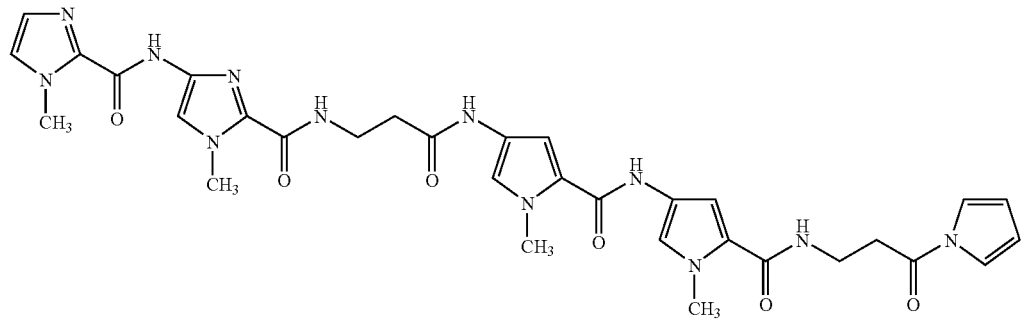

Im-Im-β-ala-Py-Py-β-ala-CO-Im': 6.3 mg (74%); $^1$H NMR (DMSO-$d_6$) δ: 3.49 (2H, q, J=6.5 Hz), 3.53 (2H, q, J=6.5 Hz), 3.78 (3H, s), 3.83 (3H, s), 3.96 (3H, s), 4.00 (3H, s), 6.83 (1H, s), 6.85 (1H, s), 7.05 (1H, s), 7.06 (1H, s), 7.15 (2H, s), 7.46 (1H, s), 7.71 (1H, s), 8.09 (1H, s), 8.23 (1H, s), 8.42 (1H, s), 8.61 (1H, s), 9.75 (1H, s), 9.84 (1H, s), 9.89 (1H, s), Four protons (2 of N—CH$_2$—C$\underline{H}_2$s) were not confirmed due to the overlap with one of the peaks of the DMSO solvent.

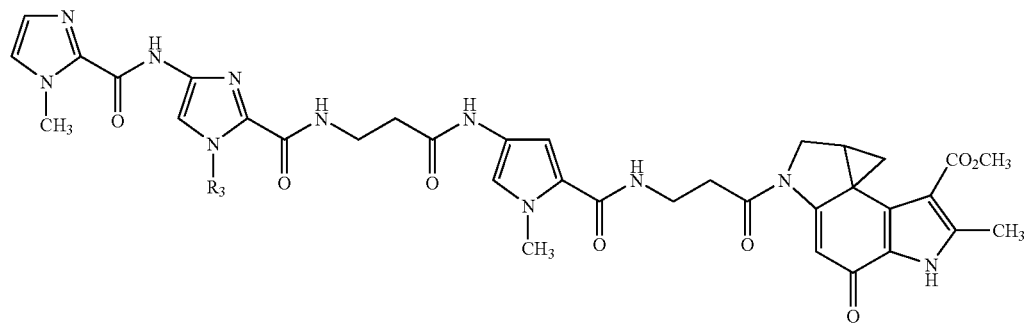

Im-Im-β-ala-Py-Py-β-ala-CO-Du86: 0.10 mg (3%); $^1$H NMR (CD$_3$OD)δ: 1.04–1.06 (1H, m), 2.08–2.12 (1H, m), 2.50 (3H, s), 2.58–2.66 (4H, m), 3.56 (2H, m), 3.67 (2H, m), 3.70–3.75 (1H, m), 3.77 (3H, s), 3.84 (3H, s), 3.87 (3H, s), 4.01 (3H, s), 4.02–4.05 (2H, m), 4.05 (3H, s), 6.74 (1H, s), 6.81 (1H, s), 7.05 (1H, s), 7.14 (2H, s), 7.25 (1H, s), 7.47 (1H, s), 7.88 (1H, s), Six protons (6 NHs) were not detected due to the conversion into CD3OD. ESI MS m/e calcd. for $C_{42}H_{46}O_9N_{13}$ (M+H) 876.3, found 876.4.

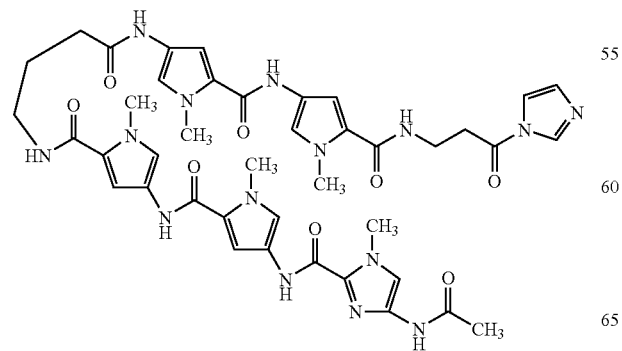

Ac-Im-Py-Py-γ-butyl-Py-Py-β-ala-CO-Im': 22.5 mg (68%); $^1$H NMR (DMSO-d$_6$) δ: 1.72–1.78 (2H, m), 2.01 (3H, s), 2.23–2.29 (2H, m), 3.50–3.56 (2H, m), 3.77 (3H, s), 3.80 (3H, s), 3.81 (3H, s), 3.84 (3H, s), 3.94 (3H, s), 6.82 (2H, s), 6.89 (1H, s), 7.03 (1H, s), 7.06 (1H, s), 7.12 (1H, s), 7.16 (1H, s), 7.26 (1H, s), 7.41 (1H, s), 7.68 (1H, s), 7.71 (1H, s), 8.00–8.04 (1H, m), 8.04–8.10 (1H, m), 8.42 (1H, s), 9.80 (1H, s), 9.82 (1H, s), 9.87 (1H, s), 9.93 (1H, s), 10.21 (1H, s), Four protons (N—CH$_2$—C$\underline{H}_2$ and N—C$\underline{H}_2$—CH$_2$) were not confirmed due to the overlap with one of the peaks of the DMSO solvent.

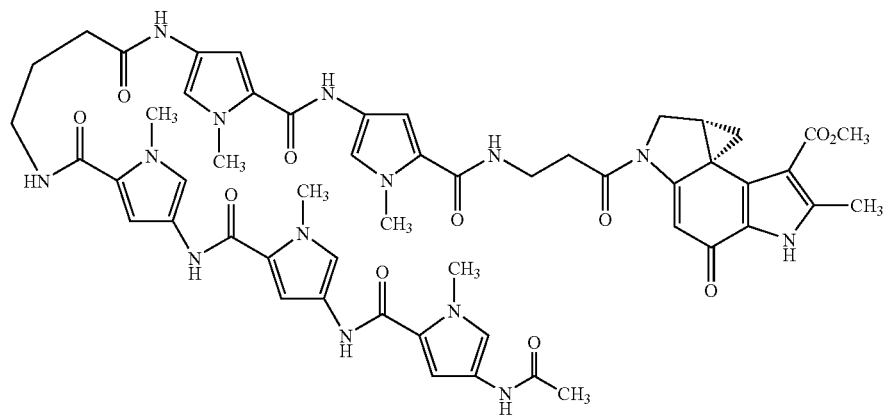

Ac-Im-Py-Py-γ-butyl-Py-Py-β-ala-CO-Du86: 0.70 mg (7% after the HPCL purification); $^1$H NMR (DMSO-d$_6$)δ: 1.04–1.06(1H, m), 2.08–2.12(1H, m), 2.58–2.66(4H, m), 3.56(2H, m), 3.67(2H, m), 3.77(3H, s), 3.84(3H, s), 3.87 (3H, s), 4.01(3H, s), 4.02–4.05(2H, m), 4.05(3H, s), 6.74 (1H, s), 6.81(1H, s), 7.05(1H, s), 7.14(1H, s), 7.47(1H, s), 7.88(1H, s), Six protons (N—CH$_2$—CH$_2$ and N—C$\underline{H}_2$—CH$_2$—CH$_2$) were not confirmed due to the conversion into CD$_3$OD. ESI MS m/e calcd. for C$_{52}$H$_{58}$O$_{11}$N$_{15}$ (M+H) 1068.3, found 1068.4.

Example 4

Sequence-Specific DNA Alkylation by Pyrrole-Imidazole Polyamide to which DNA Alkylation Agent is Transferred (1) An DNA alkylation experiment was conducted using the above-synthesized Ac-Im-Py-β-ala-CO-Du86. Results of the experiment are shown in FIG. 1.

As is apparent from FIG. 1, it was clarified that the present compound recognized 5'-TAAA-3' and alkylated adenine of 3'-end.

Figure 2:
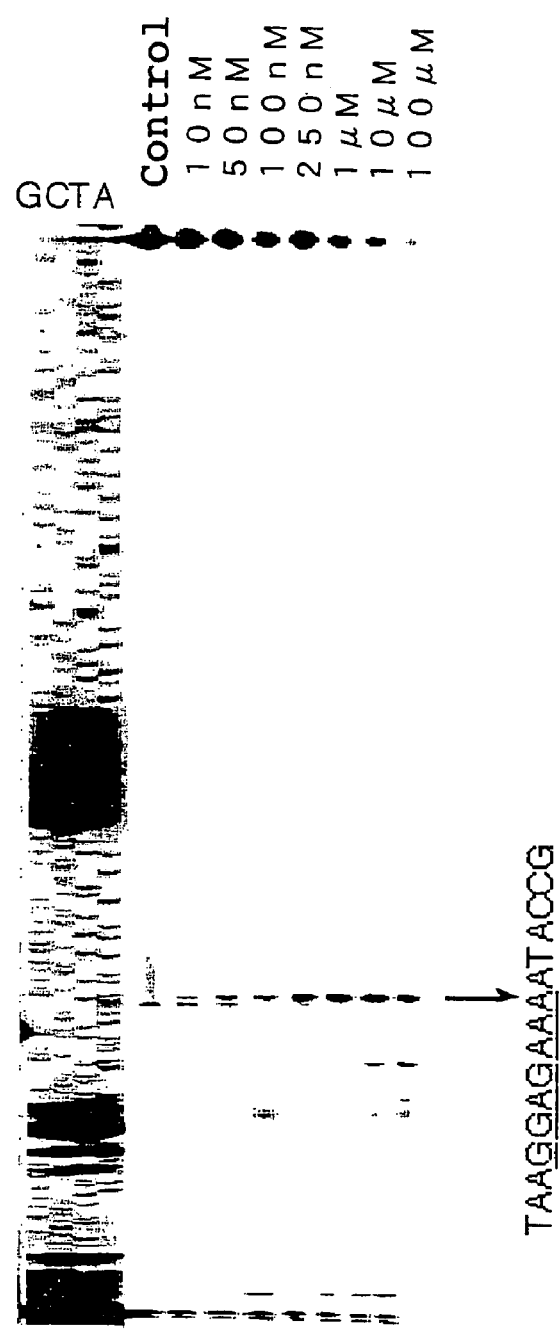
FIG. 2 shows a result of analyzing a reactivity of a DNA alkylation agent to a DNA by polyacrylamide gel electrophoresis using a DNA fragment of 450 mer in a DNA alkylation experiment of Example 4(2).

(2) A similar experiment was conducted by using Im-Im-β-ala-Py-Py-β-ala-CO-Du86. Results of the experiment are shown in FIG. 2. In this case, it was clarified that two imidazole portions recognized guanine in a DNA to cause a sequence-specific DNA alkylation. More specifically, it was clarified that the present compound recognized 5'-GGAGAAA-3' and alkylated adenine of 3'-end.

From these results, it is apparent that the compound which alkylates a DNA in a sequence-specific manner can be obtained readily by employing the present inventors' automatic synthesis of pyrrole-imidazole polyamide by the Fmoc method. According to this technique, a progress in developments of drugs targeting DNAs specific to cancer cells, i.e., developments of anti-cancer drugs with less adverse side effects is greatly expected.

Figure 3:
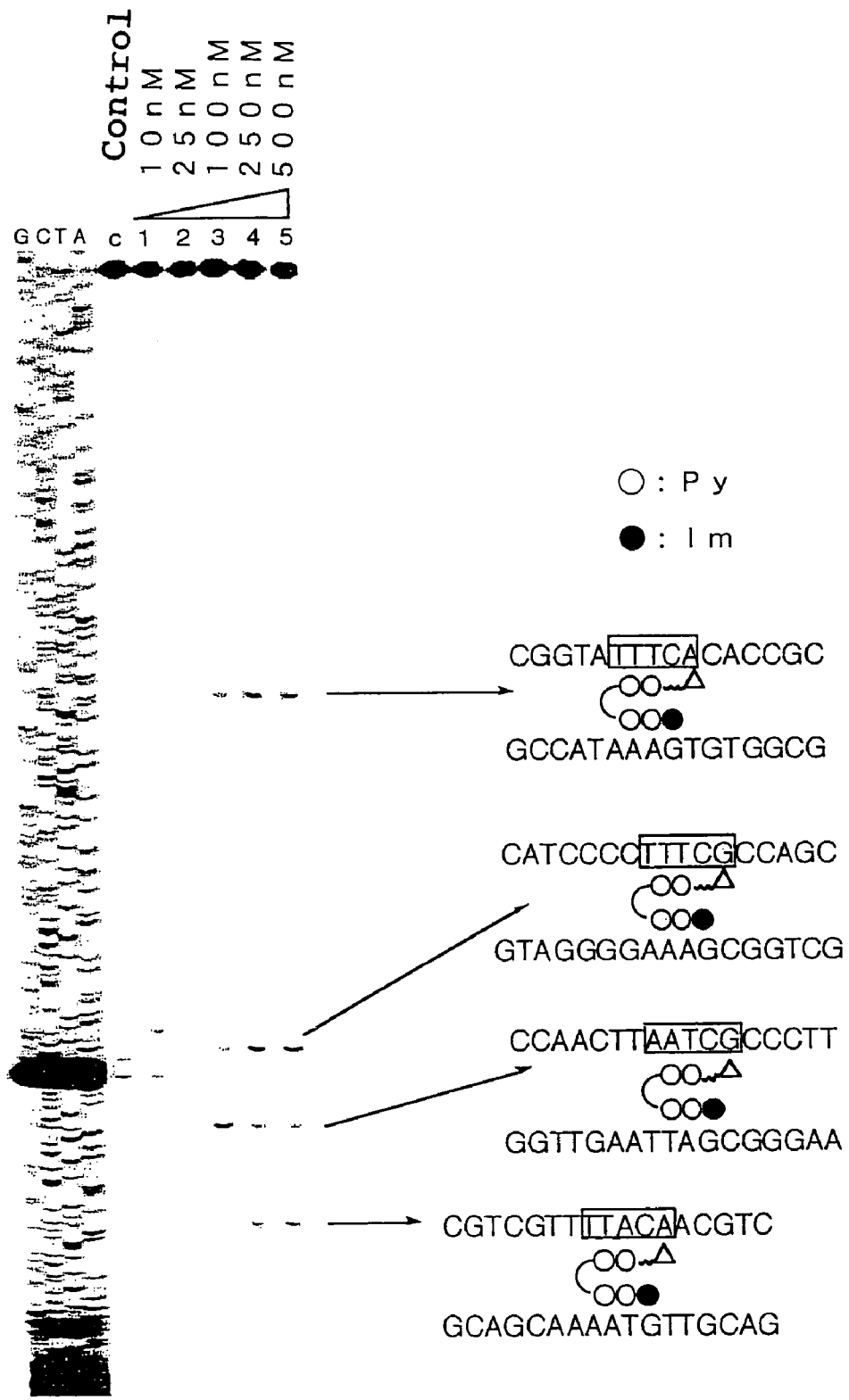
FIG. 3 shows a result of analyzing a reactivity of a DNA alkylation agent to a DNA by polyacrylamide gel electrophoresis using a DNA fragment of 450 mer in a DNA alkylation experiment of Example 4(3).

(3) A similar experiment was conducted by using Ac-Im-Py-Py-γ-butyl-Py-Py-β-ala-Du86. A pyrrole-imidazole polyamide portion of this compound has a hairpin structure, and one molecule of this compound can recognize both of double strands of a DNA. Though it is known that a Py-Py pair selectively recognizes AT or TA, a Im-Py pair selectively recognizes GC, and a Py-Im pair selectively recognizes CG when the hairpin compound is combined with a DNA in accordance with the Dervan's rule, this compound includes a new pair of β-alanine pair-Im for the molecular recognition. Therefore, a new molecular recognition rule can be discovered using this compound. Accordingly, a DNA alkylation experiment was conducted to confirm the possibility. Results of the experiment are shown in FIG. 3 (DNA: pUC18III 70 nM; Reagent Concentration: 10 nM to 500 nM, 5 samples; Reaction Conditions: sodium phosphate buffer solution (1.46 mM), 37° C., 8 hours).

As is apparent from FIG. 3, it was found that this compound alkylated the DNA with the hairpin structure in accordance with one rule. More specifically, a γ-butyl hairpin curve portion recognized AT, a Py-Py pair recognized At or TA, and Du86 alkylated A or G. In this case, the new molecular recognition pair β-alanine pair-Im pair selectively recognized a CG pair to reveal that it contributes significantly to the sequence-specific alkylation, which is the new discovery that have never been reported.

Consequently, it was found that Ac-Im-Py-Py-γ-butyl-Py-Py-β-ala-Du86 recognizes 5'-(A/T)(A/T)(A/T)C(A/G)-3' portion to selectively alkylates adenine of the 3'-end. As described above, the pyrrole-imidazole polyamide having a β-alanine carboxylic acid group at its end can readily be prepared by the method developed by the present inventors employing a peptide synthesizer. From this discovery, it was clarified that the synthesis of the present invention remarkably contributes to a synthesis of a novel DNA recognition compound.

Example 5

Solid Phase Synthesis of FITC-Pyrrole-Imidazole Polyamide Conjugate

The synthesis was performed in the same manner as in the above-described solid phase synthesis of pyrrole-imidazole polyamide, i.e., by using Pioneer (product of Applied Biosystems) which is the peptide synthesizer employing the Continuous Flow Method. Used as a solid phase carrier was a commercially available Wang resin to which Fmoc-β-alanine is preloaded. Four equivalent amounts of each of HATU, DIEA, FITC and the monomer units are used with respect to an active end of the solid phase carrier. After termination of the reaction, the solid phase carrier was taken out from the column to be subjected to a drying under reduced pressure and then moved to a 50 ml curved flask. 5 ml of the solution containing 95% TFA, 2.5% TIS, and 2.5% water was added to the solid phase carrier to be stirred for 30 minutes, whereby excising the polyamide from the carrier. Purification was performed by HPLC using a 0.1% TFA solution and acetonitrile.

A structural formula, a yield, and various spectrum data of the thus-obtained FITC-pyrrole-imidazole polyamide conjugate are shown below.

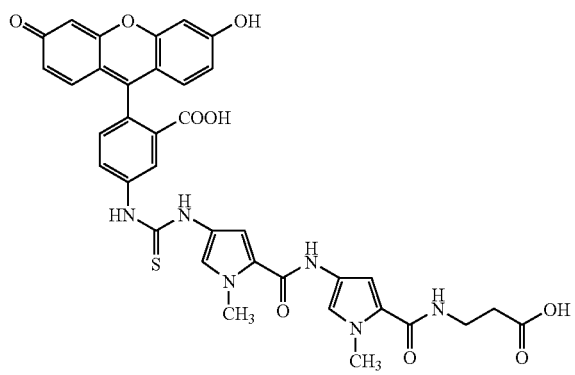

FITC-py-py-β-ala-COOH: yield 14%; $^1$H NMR (DMSO-$d_6$) δ: 3.79 (3H, s), 3.87 (3H, s), 6.54–6.62 (5H, m), 6.66 (1H, s), 6.67 (1H, s), 6.83 (1H, s), 6.97 (1H, s), 7.17 (1H, d, J=8.0 Hz), 7.18 (1H, d, J=1.5 Hz), 7.24 (1H, br. s), 7.82 (1H, dd, J=8.0, 1.5 Hz), 7.80 (1H, t, J=6.0 Hz), 8.21 (1H, s), 9.82 (1H, s), 9.85 (1H, s), 10.09 (2H, s), 12.20 (1H, br. s), Four protons (N—$CH_2$—$CH_2$—COO) were not confirmed due to the overlap with the peak of the DMSO solvent. ESI MS m/e calcd. for $C_{36}H_{31}O_6N_9S$(M+H) 723.2, found 723.2.

INDUSTRIAL APPLICABILITY

According to the method of the present invention, since it is possible to excise the end from a solid phase carrier as a carboxylic acid residue, various functional groups can be transferred into a pyrrole-imidazole polyamide. For example, it is possible to transfer duocarmycin, pyrrolobenzodiazepin, bleomycine enediyne compounds, nitrogen mustard, and their derivatives, all having the DNA alkylation ability. In short, a compound which alkylates a DNA in a sequence-specific manner can readily be obtained by the method of the present invention. According to this technique, a progress in developments of drugs targeting DNAs specific to cancer cells, i.e., developments of anti-cancer drugs with less adverse side effects is greatly expected. Further, according to the present invention, it is possible to synthesize a conjugate of a natural protein and a pyrrole-imidazole polyamide as well as a conjugate of a non-natural protein and a pyrrole-imidazole polyamide. Yet further, since the reaction conditions of the Fmoc method are less strict than those of the t-BOC method, it is possible to transfer organic compounds, in addition to the proteins, having a functional group which becomes unstable under a acidic condition and, therefore, the invention has a wider range of applicability. For example, it is possible to automatically synthesize the conjugates of a pyrrole-imidazole polyamide and DNA, RNA, or a derivative thereof.

Also, it is possible to synthesize a conjugate by transferring FITC into a pyrrole-imidazole polyamide, and the conjugate to be obtained is usable as a fluorescent labeling reagent capable of recognizing a specific DNA sequence such as a DNA sequence relating to a genetic disease such as cancer. Such conjugate can be used not only in a stage preceding a treatment with the pyrrole-imidazole polyamide, but also as a diagnostic drug.

The invention claimed is:

1. A method of synthesizing a pyrrole-imidazole polyamide comprising performing a solid phase automatic peptide synthesis via a peptide synthesizer with a resin bound to a C-terminal of a β-alanine residue or a γ-aminobutyric acid residue by a Fmoc method with HATU[O-(7-azobenzotriazole-1-yl)-1,1,3,3-tetramethyluronium hexafluorophosphate]/DIEA(N,N-diisopropylethylamine).

2. The synthesis method according to claim 1, wherein an aminopyrrole carboxylic acid where the amino group is protected with Fmoc, an aminoimidazole carboxylic acid where the amino group is protected with Fmoc, and a solid phase carrier carrying β-alanine where the amino group is protected with Fmoc or γ-aminobutyric acid where the amino group is protected with Fmoc are used.

3. The synthesis method according to claim 2, wherein the aminopyrrole carboxylic acid where the amino group is protected with Fmoc is 4-amino-1-methyl-2-pyrrole carboxylic acid, and the aminoimidazole carboxylic acid where the amino group is protected with Fmoc is 4-amino-1-methyl-2-imidazole carboxylic acid.

4. A pyrrole-imidazole polyamide having β-alanine residue or γ-aminobutyric acid residue at its C-terminal end.

5. The pyrrole-imidazole polyamide according to claim 4, wherein the pyrrole-imidazole polyamide is synthesized by using an aminopyrrole carboxylic acid where the amino group is protected with Fmoc, an aminoimidazole carboxylic acid where the amino group is protected with Fmoc, and a solid phase carrier carrying β-alanine where the amino group is protected with Fmoc or γ-aminobutyric acid where the amino group is protected with Fmoc and by automatic synthesis by a solid phase Fmoc method with the use of a HATU[O-(7-azobenzotriazole-1-yl)-1,1,3,3-tetramethyluronium hexafluorophosphate]/DIEA(N,N-diisopropylethylamine) system.

6. The pyrrole-imidazole polyamide according to claim 5, wherein the aminopyrrole carboxylic acid where the amino group is protected with Fmoc is 4-amino-1-methyl-2-pyrrole carboxylic acid, and the aminoimidazole carboxylic acid where the amino group is protected with Fmoc is 4-amino-1-methyl-2-imidazole carboxylic acid.

7. A pyrrole-imidazole polyamide obtainable by transferring a DNA alkylation agent into a carboxyl group at the end of the pyrrole-imidazole polyamide defined in claim 4.

8. The pyrrole-imidazole polyamide according to claim 7, wherein the DNA alkylation agent is an A ring (Du86) which is an active center of DU-86 (2-methyl-3-methoxycarbonyl-A ring pyrrole-DUMA).

9. A sequence-specific DNA alkylation method characterized by using the pyrrole-imidazole polyamide defined in claim 7 or 8 into which the DNA alkylation agent is transferred, said method comprising contacting said pyrrole-imidazole polyamide with the DNA.

10. The sequence-specific DNA alkylation method according to claim 9, wherein the DNA alkylation agent is an A ring (Du86) which is an active center of DU-86 (2-methyl-3-methoxycarbonyl-A ring pyrrole-DUMA).

11. A FITC (fluorescein isothiocyanate)-pyrrole-imidazole polyamide conjugate having β-alanine residue or γ-aminobutyric acid residue at its C-terminal end.

12. The synthesis method according to any one of claims 1, 2, and 3, wherein, after the synthesis by the automatic synthesis, an excision from the solid phase carrier is performed with the use of trifluoroacetic acid, triisopropylsilane, and water.

* * * * *